United States Patent [19]

Monbaliu et al.

[11] 4,062,683

[45] Dec. 13, 1977

[54] PHOTOGRAPHIC MATERIAL CONTAINING 3-ANILINO-5-PYRAZOLYLALKYLCARBONATE OR ARYLCARBONATE COUPLERS

[75] Inventors: Marcel Jacob Monbaliu, Mortsel; Raphaël Karel Van Poucke, Berchem; Roger Henri Vrydaghs, Ekeren, all of Belgium; Hans-Heinrich Credner; Ernst Meier, both of Munich, Germany

[73] Assignee: AGFA-GEVAERT N.V., Mortsel, Belgium

[21] Appl. No.: 690,584

[22] Filed: May 27, 1976

[30] Foreign Application Priority Data

May 30, 1975 Germany .............................. 2523882

[51] Int. Cl.$^2$ .......................... G03C 7/00; G03C 1/40
[52] U.S. Cl. ................................ 96/56.5; 96/100 R; 548/360

[58] Field of Search .................................. 96/100, 56.5

[56] References Cited

U.S. PATENT DOCUMENTS

| T887,007 | 6/1971 | Dallon et al. ........................ 96/100 |
| 2,476,986 | 7/1949 | Martin ................................. 96/100 |
| 2,575,182 | 11/1951 | Martin ................................. 96/100 |
| 2,865,748 | 12/1958 | Feniak et al. ......................... 96/56.5 |
| 3,926,631 | 12/1975 | Arai et al. ............................. 96/74 |

*Primary Examiner*—J. Travis Brown
*Attorney, Agent, or Firm*—A. W. Breiner

[57] ABSTRACT

3-Anilino-5-pyrazolyl alkylcarbonates and arylcarbonates are described for use in silver halide color photography as color coupler precursor compounds containing no active methylene group so that they do not take part in undesirable side-reactions before color development.

5 Claims, No Drawings

PHOTOGRAPHIC MATERIAL CONTAINING 3-ANILINO-5-PYRAZOLYLALKYLCARBONATE OR ARYLCARBONATE COUPLERS

The present invention relates to 3-anilino-5-pyrazolyl alkyl carbonates or aryl carbonates, to the preparation thereof and their use in light-sensitive colour elements.

The formation of coloured photographic images by the coupling of oxidized aromatic primary amino developing agents with colour couplers is well known. In these processes the subtractive process of colour formation is ordinarily used and the image dyes are intended to be cyan, magenta, and yellow, being the colours complementary to the primary colours. Usually, phenol or naphthol couplers are used to form the cyan dye image, 2-pyrazolin-5-one couplers to form the magenta dye image, and couplers containing a methylene group having one or two carbonyl groups attached to it to form the yellow dye image.

It is known e.g. from the U.S. Pat. Nos. 2,575,182 and 2,865,748 and from the U.S. Defensive Publication T 887,007 to use 5-enol esters of 2-pyrazolin-5-one colour couplers. These 5-acyloxypyrazole couplers are obtained by acylation of the corresponding 2-pyrazolin-5-one couplers with an acid choride or anhydride. Although the 5-acyloxypyrazole compounds no longer contain a reactive methylene group in the 4-position, they can couple with the oxidized developing agent and form a dye by reformation of the free 2-pyrazolin-5-one coupler through splitting off of the acid radical prior to or simultaneously with the colour development. These couplers have the advantage that they cannot take part in any undesirable side-reaction before the colour development because of the presence of an inactive methylene group.

The 5-enol esters of 2-pyrazolin-5-one couplers having an alkyl-, aryl-, or acylamino group in the 3-position can easily be prepared whereas the 2-pyrazolin-5-one couplers having an anilino group in the 3-position, which as magenta colour couplers are particularly advantageous, can hardly be converted into the 5-enol esters by acylation.

When chloroformiates are used as acylating agents, it is impossible, even in the presence of a base, to prepare the 3-anilino-5-pyrazolyl-alkyl carbonates or aryl carbonates. Yet, 5-pyrazolyl-alkyl carbonates or aryl carbonates are advantageous precursors of 2-pyrazolin-5-one colour couplers because the oxycarbonyl groups, especially the aryloxycarbonyl groups readily split off.

It is an object of the invention to prepare 3-anilino-5-pyrazolyl-alkyl carbonates or aryl carbonates by reaction with chloroformiates. These carbonates can be used as colour couplers or as precursors of colour couplers in photographic materials.

The present invention thus provides as novel compounds 3-anilino-5-pyrazolyl-alkyl carbonates or -aryl carbonates according to the following general formula:

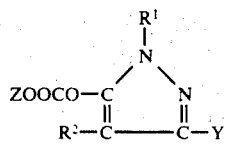

wherein:

Z represents alkyl including substituted alkyl or aryl including substituted aryl e.g. methyl, ethyl, trichloroethyl, propyl, butyl, benzyl, phenyl, sulphophenyl, alkoxycarbonylphenyl, etc.

Y represents an anilino group common in 2-pyrazolin-5-one colour couplers e.g. anilino carrying one or more substituents e.g. alkyl, alkoxy, alkylthio, aryloxy, halogen e.g. chloro, nitro, cyano, sulpho, amino, substituted amino, e.g. acylamino such as carboxyl- or sulphonacylamino, sulphamyl, carbamyl etc., and each of $R^1$ and $R^2$ a group common in 2-pyrazolin-5-one colour couplers, which carbonates can be prepared by reaction of the corresponding 3-anilino-2-pyrazolin-5-one with a chloroformiate according to the formula:

ZOOCCl in which Z has the significance described above, at a temperature below $-20°$ C, preferably below $-40°$ C, in the presence of a strong organic base with a pKb-value of at most 5, e.g. in the presence of an aliphatic tertiary amine, preferably triethylamine.

$R^1$ preferably represents (1) an alkyl group, e.g. $C_1$-$C_{22}$ alkyl, preferably $C_1$  $C_5$ alkyl, which may be substituted e.g. 2,2,2-trifluoroethyl, cyanoethyl, benzyl and substituted benzyl, e.g. chlorobenzyl etc. or (2) an aryl group e.g. phenyl, which may carry one or more substituents, which include alkyl e.g. methyl, halogen, e.g. chlorine and bromine, sulpho, carboxy, alkoxy e.g. methoxy, phenoxy, alkylsulphonyl e.g. methylsulphonyl, alkylthio e.g. methylthio, carbalkoxy, haloalkoxy, haloalkylthio, haloalkylsulphonyl, sulphamoyl, carbamoyl, cyano, nitro, etc., $R^2$ preferably represents (1) hydrogen, (2) a group that can be split off during colour development such as halogen e.g. chloro, a sulpho group in acid or salt form, alkoxy e.g. methoxy, aryloxy e.g. phenoxy, acyloxy, an alkylthio group, an arylthio group, e.g. phenylthio, a heterocyclic thio group e.g. 1-phenyl-5-tetrazolylthio, 2-benzothiazolylthio, and 2-benzimidazolylthio, an arylazo group e.g. phenylazo, chlorophenylazo, and methoxyphenylazo, or a benzotriazolyl group or an alkyl group including a substituted alkyl group, preferably having 1-5 carbon atoms, e.g. methyl as in the known 2-pyrazolin-5-one competing couplers.

The reaction of the 3-anilino-2-pyrazolin-5-one colour coupler with the chloroformiate is carried out preferably in an organic solvent e.g. dichloromethane, acetonitrile, dioxan, etc. The molar proportion between pyrazolinone and ester advantageoulsy ranges between 1:1 and 1:5, the molar proportion between pyrazolinone and organic base ranging between 1:1 and 1:5 as well.

It is obvious that preferred substituents can be introduced into the groups $R^1$, $R^2$, and Y prior or subsequent to the conversion according to known chemical methods.

The following examples illustrate the preparation of the compounds according to the invention.

The structures of the compounds are determined by IR and NMR spectrometry. The alkyl and aryl-5-pyrazolyl carbonates differ from the 2-aryloxycarbonyl or 2-alkoxycarbonyl-3-pyrazolin-5-ones by 1. the IR-absorption frequency (in dichloromethane) of the carbonyl group, i.e. 5.70–5.80 μm in the case of the 2-acylated compounds and 5.55–5.60 μm in the case of the 5-acylated compounds, and 2. the chemical shift (in CDCl$_3$) of the C-proton of the 4-position, i.e. in the case of 2-acylated compounds less than 6 ppm and in the case of 5-acylated compounds more than 6 ppm as compared with tetraethylsilane.

Preparation 1

1-(2,4,6-trichlorophenyl)-3-{2-chloro-5-[α-methyl-β-(2-cyclopentyl-4-t-butyl-phenoxy)-ethoxycarbonylamino]-anilino}-5-pyrazolyl-phenylcarbonate.

11.75 g (0.075 mole) of phenylchloroformiate are added dropwise in 15 min to a solution, cooled to −60° C, of 35.3 g (0.05 mole) of the corresponding 3-anilino-2-pyrazolin-5-one and 10.35 ml (0.075 mole) of triethylamine in 100 ml of dichloromethane. Care must be taken that the temperature remains below −60° C. After 15 min 0.1 N of hydrochloric acid is poured in the dichloromethane layer. Subsequently the mixture is washed with ice-water until free from acid. After drying the solvent is removed by evaporation and the residue is stirred with hexane. The precipitate is filtered off. Yield: 24 g (58%). Melting point: 70° C.

Structural analysis

IR: $\gamma_{CO}$ 5.56 μm
NMR: $\delta_{-CH=}$ 6.28 ppm

Preparation 2

1-(2,6-dichloro-4-methylsulfphonylphenyl)-3-(2-chloro-5-N-methyl-N-hexadecylsulphamoylanilino)-5-pyrazolyl-phenylcarbonate 11.75 g (0.075 mole) of phenyl chloroformiate are added dropwise in 5 min to a solution of 37.5 g (0.05 mole) of 1-(2,6-dichloro-4-methylsulphonylphenyl)-3-(2-chloro-5-N-methyl-N-hexadecylsulphamoyl)-2-pyrazolin-5-one and 10.35 ml (0.075 mole) of triethylamine in 120 ml of dichloromethane, which solution had been cooled to −70° C by means of acetone and carbon dioxide. Care must be taken that the temperature remains beneath −60° C. After 30 min the dichloromethane solution is poured into 1 N hydrochloric acid. The dimethylene layer is washed until free from acid, dried, and concentrated by evaporation. The resulting oil is stirred in hexane and the precipitate obtained is filtered off. Yield: 30 g (69%). Melting point: 75° C.

Structural analysis

IR: $\gamma_{CO}$ 5.55 μm
NMR: $\delta_{-CH=}$ 6.20 ppm

Preparation 3

1-(2,4,6-trichlorophenyl)-3-(2-chloro-5-myristoylaminoanilino)-4-chloro-5-pyrazolyl-ethylcarbonate 4.3 ml (0.045 mole) of ethyl chloroformiate are added dropwise in 15 min to a solution cooled to −50° C of 19.5 g (0.03 mole) of 1-(2,4,6-trichlorophenyl)-3-(2-chloro-5-myristoylanilino)-4-chloro-2-pyrazolin-5-one and 6.2 ml (0.045 mole) of triethylamine in 50 ml of dichloromethane. After 30 min 3 ml of acetic acid are added, whereupon the solution is washed thrice with water. The solution is dried and concentrated by evaporation. An oily residue remains.

Structural analysis

IR: $\gamma_{CO}$ 5.57 μm

Preparation 4

1-(2,4,6-trichlorophenyl)-3-(2-chloro-5-myristoylaminoanilino)-5-pyrazolyl-2,2,2-trichloroethylcarbonate In accordance with the process of preparation 2,26.5 g (67%) of the above compound melting at 70° C are obtained from 30.7 g (0.05 mole) of 1-(2,4,6- trichlorophenyl)-3-(2-chloro-5-myristoylaminoanilino)-2-pyrazolin-5-one and 11.7 ml (0.075 mole) of 2,2,2-trichloroethoxycarbonyl chloride in 120 ml of dichloromethane and in the presence of 10.35 ml of triethylamine (0.075 mole).

Structural analysis

IR: $\gamma_{CO}$ 5.564 μm
NMR: $\delta_{-CH=}$ 6.25 ppm

Preparation 5

1-(2,4,6-trichlorophenyl)-3-(2-chloromyristoylaminoanilino)-5-pyrazolylphenylcarbonate In accordance with the process of preparation 2, 11 g (50%) of the above compound melting at 86° C are obtained from 18.4 g (0.03 mole) of 1-(2,4,6-trichlorophenyl)-3-(2-chloro-5-myristoylaminoanilino)-2-pyrazolin-5-one and 5.67 ml (0.045 mole) of phenyl chloroformiate in 80 ml of dichloromethane in the presence of 6.2 ml (0.045 mole) of triethylamine.

Structural analysis

IR: $\gamma_{CO}$ 5.55 μm
NMR: $\delta_{-CH=}$ 6.22 ppm

Preparation 6

1-(2,6-dichloro-4-methylsulphonylphenyl)-3-(2-chloro-5-N-methyl-N-hexadecylsulphamoylanilino)-5-pyrazolyl-ethylcarbonate was prepared in a similar way as the phenyl carbonate of preparation 2.
Yield: 56%. Melting point: 78° C.

Structural analysis

IR: $\gamma_{CO}$ 5.59 μm
NMR: $\delta_{-CH=}$ 6.25 ppm

The 3-anilino-5-pyrazolyl-alkyl carbonates or -aryl carbonates according to the invention can be used as coloured or uncoloured couplers as well as in the form of competing couplers in photographic silver halide colour materials.

Because of the inactive methylene group these couplers cannot participate in any undesirable side reactions with other emulsion ingredients e.g. traces of aldehyde hardening agents such as formaldehyde and mucochloric acid during manufacture and storage, which would result in a reduction of the amount of coupler available for coupling with the oxidized developing agent and thus in a reduction of colour density, the production of stains, etc. The coupling reaction in alkaline medium, however, is more powerful than these side-reactions and splits off the alkoxy- or aryloxycarbonyl group, thus leading to the formation of free 2-pyrazolin-5-one coupler available for coupling.

The present invention thus also provides a photographic colour material comprising a support and at least one silver halide emulsion layer, containing a 3-anilino-5-pyrazolyl alkyl carbonate or -aryl carbonate as coupler, especially a precursor of a coupler according to the above general formula. Couplers corresponding to the above general formula for use in photographic silver halide emulsions generally comprise in $R^1$ or preferably in Y a ballasting group rendering fast to diffusion and comprising an aliphatic straight-chain or branched-chain hydrocarbon group of at least 5 carbon atoms.

The non-diffusing couplers according to the invention can be incorporated into the photographic silver halide material according to any suitable technique known in the art. The couplers of the invention are preferably incorporated into photographic hydrophilic colloid media from solutions in high-boiling sparingly water-miscible solvents such as di-n-butyl phthalate and tricresyl phosphate or in low-boiling, sparingly water-miscible solvents such as ethyl acetate, methylene chloride, diethyl carbonate, chloroform, etc., or mixtures thereof.

For this purpose these solutions can be dispersed in extremely fine droplets, preferably in the presence of one or more wetting or dispersing agents into a hydrophilic colloid medium e.g. aqueous gelatin or into water, the low-boiling, sparingly water-miscible solvent then being removed by evaporation. The stable dispersions of the couplers can be stored as such and then admixed whenever desired with the very coating composition of the hydrophilic colloid layer such as a silver halide emulsion layer into which the compounds are intended to be present.

It is obvious that the compounds of the invention can also be incorporated in other ways into the hydrophilic colloid media.

More details about particularly suitable techniques that can be employed for incorporating the couplers of the invention into a hydrophilic colloid layer of a photographic material there can be referred to e.g. U. S. Pat. Nos. 2,269,158 — 2,284,887 — 2,304,939 — 2,304,940 and 2,322,027, United Kingdom patent specification Nos. 791,219 — 1,098,594 — 1,099,415 — 1,099,416 — 1,099,417 — 1,218,189 — 1,272,561 — 1,297,347, and 1,297,947, French Pat. No. 1,555,663, Belgian Pat. No. 722,026, and German Pat. No. 1,127,714.

The couplers according to the invention can be used in conjunction with various kinds of photographic emulsions. Various silver salts can be used as the sensitive salt such as silver bromide, silver iodide, silver chloride, or mixed silver halides such as silver chlorobromide, silver bromoiodide, and silver chlorobromoiodide. The couplers can be used in emulsions of the mixed packet type as described in U.S. Pat. No. 2,698,794 or emulsions of the mixed grain type as described in U.S. Pat. No. 2,592,243. The couplers can be used with emulsions, in which latent images are formed predominantly at the surface of the silver halide crystal, or with emulsions, in which latent images are formed predominantly inside the silver halide crystal.

The hydrophilic colloid used as the vehicle for the silver halide may be e.g. gelatin, colloidal albumin, zein, casein, a cellulose derivative, a synthetic hydrophilic colloid such as polyvinyl alcohol, poly-N-vinyl pyrrolidone, etc. If desired, compatible mixtures of two or more of these colloids can be employed for dispersing the silver halide.

The light-sensitive silver halide emulsions of use in the preparation of a photographic material according to the present invention can be sensitized chemically as well as spectrally. They can be chemically sensitized by effecting the ripening in the presence of small amounts of sulphur-containing compounds such as allyl thiocyanate, allyl thiourea, sodium thiosulphate, etc. The emulsions can also be sensitized by means of reductors, e.g. tin compounds as described in French Pat. No. 1,146,955 and in Belgian Pat. No. 568,687, imino-amino methane sulphinic acid compounds as described in United Kingdom patent specification No. 789,823 and small amounts of noble metal compounds such as gold, platinum, palladium, iridium, ruthenium, and rhodium compounds. They can be spectrally sensitized by means of cyanine and merocyanine dyes.

The said emulsions can also comprise compounds that sensitize the emulsions by development acceleration, e.g. compounds of the polyoxyalkylene type such as alkylene oxide condensation products as described i.a. in U.S. Pat. Nos. 2,531,832 — 2,533,990 — 3,210,191, and 3,158,484, in United Kingdom patent specifications Nos. 920,637 and 991,608 and in Belgian Pat. No. 648,710 and onium derivatives of amino-N-oxides as described in United Kingdom patent specification No. 1,121,696.

Further, the emulsions may comprise stabilizers e.g. heterocyclic nitrogen-containing thioxo-compounds such as benzothiazoline-2-thione and 1-phenyl-2-tetrazoline-5-thione and compounds of the hydroxytriazolopyrimidine type. They can also be stabilized with mercury compounds such as the mercury compounds described in Belgian Pat. Nos. 524,121 — 677,337, and 707,386, and in U.S. Pat. No. 3,179,520.

The light-sensitive emulsions may also comprise any other type of ingredient such as plasticizers, hardening agents, wetting agents, etc.

The non-diffusing magenta-forming couplers described in the present invention are usually incorporated into the green-sensitized silver halide emulsion for forming one of the differently sensitized silver halide emulsion layers of a photographic multilayer colour material. Such photographic multilayer colour material usually comprises a support, a red-sensitized silver halide emulsion layer with a cyan colour coupler, a green-sensitized silver halide emulsion layer with a magenta colour coupler, and a blue-sensitive silver halide emulsion layer with a yellow colour coupler.

The emulsions can be coated on a wide variety of photographic emulsion supports. Typical supports include cellulose ester film, polyvinylacetal film, polystyrene film, polyethylene terephthalate film and related films or resinous materials, as well as paper and glass. It is also possible to employ paper coated with $\alpha$-olefin polymers e.g. paper coated with polyethylene, polypropylene, ethylene-butylene copolymers, etc.

Photographic materials comprising couplers according to the present invention can be developed with any of the known aromatic primary amino colour developing agents e.g. p-phenylene diamine and derivatives thereof, e.g. N,N-diethyl-p-phenylene diamine, N-butyl-N-sulphobutyl-p-phenylene diamine, 2-amino-5-diethylaminotoluene, 4-amino-N-ethyl-N($\beta$-methanesulphonamido-ethyl)-m-toluidine, N-hydroxyethyl-N-ethyl-p-phenylene diamine, etc.

The following examples illustrate the use of magenta couplers according to the invention.

EXAMPLE 1

117 g of a silver bromoiodide emulsion (2.3 mole % of iodide) containing an amount of silver halide equivalent to 47 g of silver nitrate as well as 73.4 g of gelatin were diluted with 192.5 g of a 7.5% aqueous gelatin solution and 200 g of distilled water. The resulting emulsion was admixed with an emulgate obtained by dissolving 0.006 mole of 1-(2,4,6-trichlorophenyl)-3-(2-chloro-5-myristoylaminoanilino)-5-pyrazolyl phenyl carbonate in 18 ml of ethyl acetate, dispersing the solution in 100 ml of a 5% aqueous gelatin solution in the presence of a dispersing agent by means of an ultrasonic power generator, and eliminating the ethyl acetate by evaporation under reduced pressure. After neutralization of the emulsion and addition of the usual additives such as e.g. stabilizing agents, and wetting agents, distilled water was added to make 720 g.

In the same way an emulsion was prepared, which instead of the acylated colour coupler contained the non-acylated colour coupler.

The emulsions obtained were coated on a cellulose triacetate support in a ratio of 125 g/sq.m. The emulsion layers were dried and coated with a gelatin protecting layer.

The dried materials were exposed for 1/20 s through a continuous wedge having a constant of 0.3 and developed subsequently for 10 min at 24° C in a developing bath having the following composition:

| 2-amino-5-diethylaminotoluene hydrochloride | 3 g |
|---|---|
| sodium hexametaphosphate | 2 g |
| anhydrous sodium sulphite | 4 g |
| anhydrous sodium carbonate | 17 g |
| potassium bromide | 2 g |
| water to make | 1 liter |

The developed materials were treated for 5 min at 24° C in an intermediate bath containing 200 g of sodium thiosulphate per liter of water, rinsed for 10 min in water, and treated in a potassium bichromate bleaching bath.

The bleached materials were rinsed for 5 min in water and fixed in an aqueous solution of 200 g of sodium thiosulphate per liter.

After a final rinsing in water of 10 min the materials were dried.

Magenta wedges having the following photographic characteristics were obtained:

| Colour coupler | Relative sensitivity | Gamma | $D_{max}$ |
|---|---|---|---|
| non-acylated | 100 | 1.20 | 1.85 |
| acrylated | 98 | 1.21 | 2.07 |

EXAMPLE 2

Example 1 was repeated with the difference that 1-(2,6-dichloro-4-methylsulphonylphenyl)-3-(2-chloro-5-N-methyl-N-hexadecylsulphamoylanilino)-5-pyrazolyl phenyl carbonate and the parent non-acylated coupler were used as colour couplers and that after exposure the materials were not only developed as described but also developed in other conventional developing baths based on other conventional colour developing agents.

The magenta wedges obtained had the following maximum density values:

| developing agent | $D_{max}$ with acylated coupler | $D_{max}$ with non-acylated coupler |
|---|---|---|
| N,N-diethyl-p-phenylene diamine | 3.15 | 2.79 |
| 2-amino-5-[N-ethyl-N(β-methylsulphonylamino)ethyl]amino toluene sulphate | 2.58 | 2.40 |
| 2-amino-5-diethylaminotoluene hydrochloride | 2.83 | 2.65 |

We claim:

1. Light-sensitive material comprising at least one silver halide emulsion layer and a 3-anilino-5-pyrazolyl carbonate according to the following general formula:

$$\text{ZOOCOC} \overset{\overset{\displaystyle R^1}{|}}{\underset{\underset{\displaystyle R^2-C}{\|}}{\diagdown}} \overset{N}{\underset{\underset{\displaystyle C-Y}{\|}}{\diagup}}$$

in which:
Z represents an alkyl or aryl group.
Y represents an anilino group,
$R^1$ represents an alkyl group having 1-22 carbon atoms, or an aryl group,
$R^2$ represents hydrogen, an alkyl group, halogen, sulpho, alkoxy, aryloxy, acyloxy, alkylthio, arylthio, a heterocyclic thio group, an arylazo group, or a benzotriazolyl group.

2. Light-sensitive material according to claim 1, wherein Y represents an anilino group carrying at least one member selected from an alkyl group, an alkylthio group, an alkoxy group, an aryloxy group, a halogen atom, a nitro group, a cyano group, a sulpho group, an amino group, a carbamyl group or a sulphamyl group.

3. Light-sensitive material according to claim 1, wherein $R^1$ represents an alkyl group substituted by halogen, cyano, or phenyl, or an aryl group substituted by one or more members selected from an alkyl group, a halogen atom, a sulpho group, an alkoxy group, a phenoxy group, an alkylsulphonyl group, an alkylthio group, a carbalkoxy group, a sulphamyl group, a carbamyl group, a cyano group, or a nitro group.

4. Process for the production of photographic colour images, by colour development of a photographic material with an aromatic, primary amino developing agent in the presence of a 3-anilino-5-pyrazolyl alkyl carbonate or aryl carbonate.

5. Process according to claim 4, wherein the 3-anilino-5-pyrazolyl carbonate corresponds to the following formula:

$$\text{ZOOCOC} \overset{\overset{\displaystyle R^1}{|}}{\underset{\underset{\displaystyle R^2-C}{\|}}{\diagdown}} \overset{N}{\underset{\underset{\displaystyle C-Y}{\|}}{\diagup}}$$

in which
Z represents an alkyl or aryl group,
Y represents an anilino group,
$R^1$ represents an alkyl group having 1-22 carbon atoms, or an aryl group,
$R^2$ represents hydrogen, an alkyl group, halogen, sulpho, alkoxy, aryloxy, acyloxy, alkylthio, arylthio, a heterocyclic thio group, an arylazo group, or a benzotriazolyl group.

* * * * *